April 12, 1949. W. B. CLARKE Plant Pat. 832
LILAC PLANT
Filed July 2, 1947
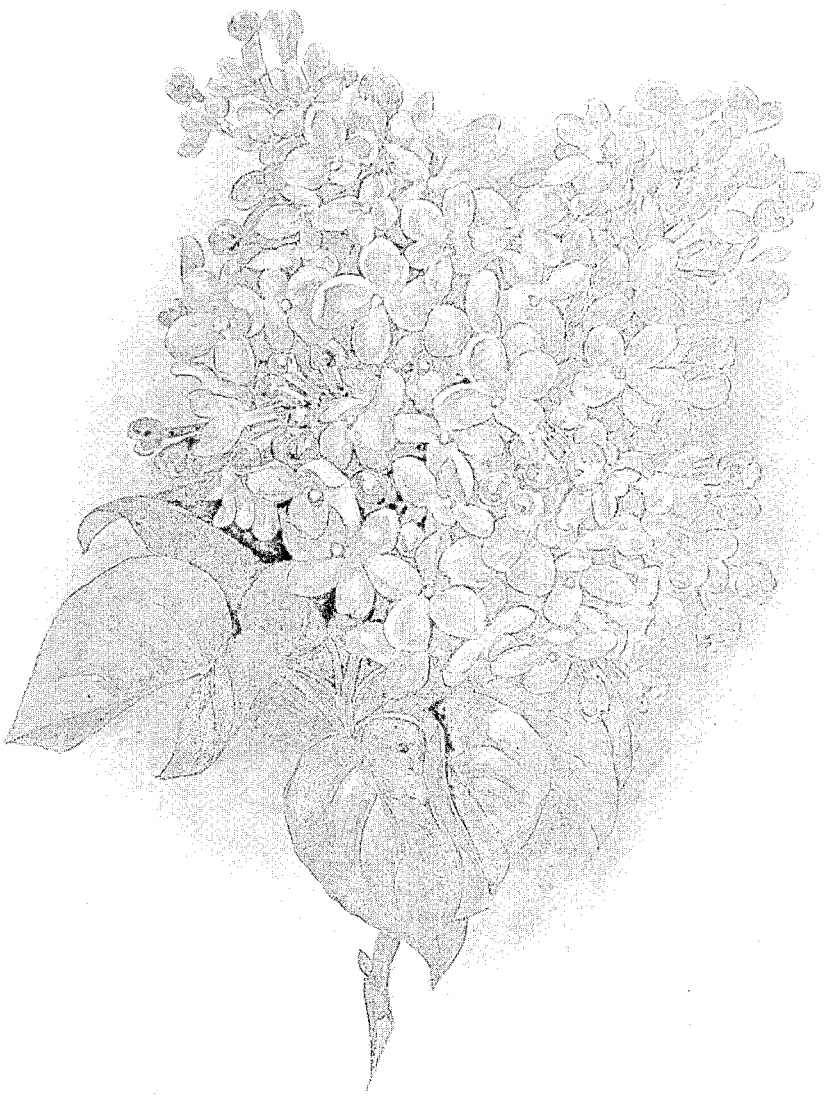
WITNESS
Addison E. Avery
INVENTOR
WALTER BOSWORTH CLARKE,
by Rummler Rummler & Snow,
ATTYS.

Patented Apr. 12, 1949

Plant Pat. 832

UNITED STATES PATENT OFFICE

832

LILAC PLANT

Walter Bosworth Clarke, San Jose, Calif., assignor to W. B. Clarke & Co., San Jose, Calif., a partnership Application July 2, 1947, Serial No. 758,625

1 Claim. (Cl. 47—60)

The present discovery relates to a new and distinct variety of *Syringa vulgaris*, the result of crossing unnamed varieties of seedlings. This new variety has been reproduced in quantity from buds and its characteristics appear to be permanently fixed.

Its novelty resides primarily in the unique deep purple coloring of the flowers, the very dark, nearly black, purple color of the buds, the great size of the florets, the large and usually unforked clusters of bloom, and its early blooming period.

The accompanying painting shows a characteristic bloom cluster of the new lilac in its natural colors.

In general plant structure, this new variety is similar to the well-known *Syringa vulgaris*. Its habit of growth is moderately vigorous; the bush is well branched and grows to a height of about eight to ten feet. It blooms profusely very early in the spring. The individual floret has four single petals and is about 1.3 inches in diameter. Its fragrance is pleasing, but usual. It has a good lasting quality, both on the plant and as a cut flower.

It can best be compared to the variety "Marceau" but its flowers are larger, and of a deeper purple color. It is also a much better bloomer than "Marceau." It will rank as one of the very earliest dark purple lilacs known to date.

The color designations according to Maerz and Paul Dictionary of Color are as follows:

| Item | Plate | Letter | No. |
|---|---|---|---|
| Open flowers | 41 | L | 5 |
| Edge of back of petals | 41 | K | 5 |
| Buds | 55 | L | 12 |
| Tipped with | 41 | L | 5 |
| Stamens | 17 | L | 3 |
| Leaf | 22 | K | 7 |
| Stems | 14 | B | 3 |

The present variety is further characterized as to novelty by the showy floriferousness of the shrubs, by its ability to begin flowering at an earlier period of the year than other dark purple lilacs, and its free branching habit.

Having thus disclosed my invention, I claim:

A new and distinct variety of *Syringa vulgaris* plant, substantially as described, being characterized by the large size of the individual floret, the dark purple color of the bloom, the very deep, almost black purple coloring of the buds, the large and usually unforked clusters of bloom, and its early period of blooming.

WALTER BOSWORTH CLARKE.

No references cited.